(12) United States Patent
Marshall

(10) Patent No.: US 6,572,562 B2
(45) Date of Patent: Jun. 3, 2003

(54) METHODS FOR MONITORING AFFECTIVE BRAIN FUNCTION

(75) Inventor: Sandra P. Marshall, San Diego, CA (US)

(73) Assignee: Eyetracking, Inc., San Diego, CA (US)

( * ) Notice: Subject to any disclaimer, the term of this patent is extended or adjusted under 35 U.S.C. 154(b) by 61 days.

(21) Appl. No.: 09/801,068

(22) Filed: Mar. 6, 2001

(65) Prior Publication Data
US 2003/0078513 A1 Apr. 24, 2003

(51) Int. Cl.[7] .............................................. A61B 13/00
(52) U.S. Cl. ...................... 600/558; 600/544; 600/545; 351/209; 351/246
(58) Field of Search ................................ 600/544, 545, 600/558; 351/205, 209, 246

(56) References Cited

U.S. PATENT DOCUMENTS

| | | | | |
|---|---|---|---|---|
| 4,012,128 A | * | 3/1977 | Regan | 351/224 |
| 4,931,865 A | | 6/1990 | Scarampi | 358/84 |
| 5,331,969 A | * | 7/1994 | Silberstein | 600/544 |
| 5,649,061 A | | 7/1997 | Smyth | 395/20 |
| 6,024,707 A | * | 2/2000 | Scinto et al. | 600/558 |
| 6,090,051 A | | 7/2000 | Marshall | 600/558 |
| 6,102,846 A | | 8/2000 | Patton et al. | 600/26 |
| 6,102,870 A | | 8/2000 | Edwards | 600/558 |
| 6,106,119 A | | 8/2000 | Edwards | 351/209 |

FOREIGN PATENT DOCUMENTS

WO    WO 99/18842    4/1999

OTHER PUBLICATIONS

Ahern and Beatty, Science (1979) 205:1289–1292.
Bradshaw, Quaterly Journal of Experimental Psychology (1968) 20:116–122.
Davidson and Sutton, Current Opinion in Neurobiology (1995) 5:217–224.
Gardner et al.; Perceptual and Motor Skills (1975) 41:951–955.
Granholm et al., Psychophysiology (1996) 33:457–461.
Hess and Polt, Science (1964) 140:1190–1192.
Kim et al., Cortex (1998) 34:753–762.
Loewenfeld, in The Pupil: Anatomy, Physiology and Clinical Applications, vol. I; Ames, Iowa, Iowa State University (1993) pp. 83–89.
Metalis et al., Journal of Applied Psychology (1980) 65:359–363.
Schluroff, Brain and Language (1982) 17:133–145.
Tomarken et al., Journal of Personlity and Social Psychology (1992) 62:676–687.

* cited by examiner

Primary Examiner—Timothy L. Maust
(74) Attorney, Agent, or Firm—Morrison & Foersterr LLP

(57) ABSTRACT

An evaluation of affective brain function and, more particularly, to the monitoring of such function as an indication of the reception of visual stimulus. Such evaluation primarily involves analyzing dilation responses as a measure of whether the visual stimulus evokes a positive or negative affective response.

12 Claims, 2 Drawing Sheets high level of attraction
(cumulative levels of dilation)

Time (each tick mark equals 1 second)

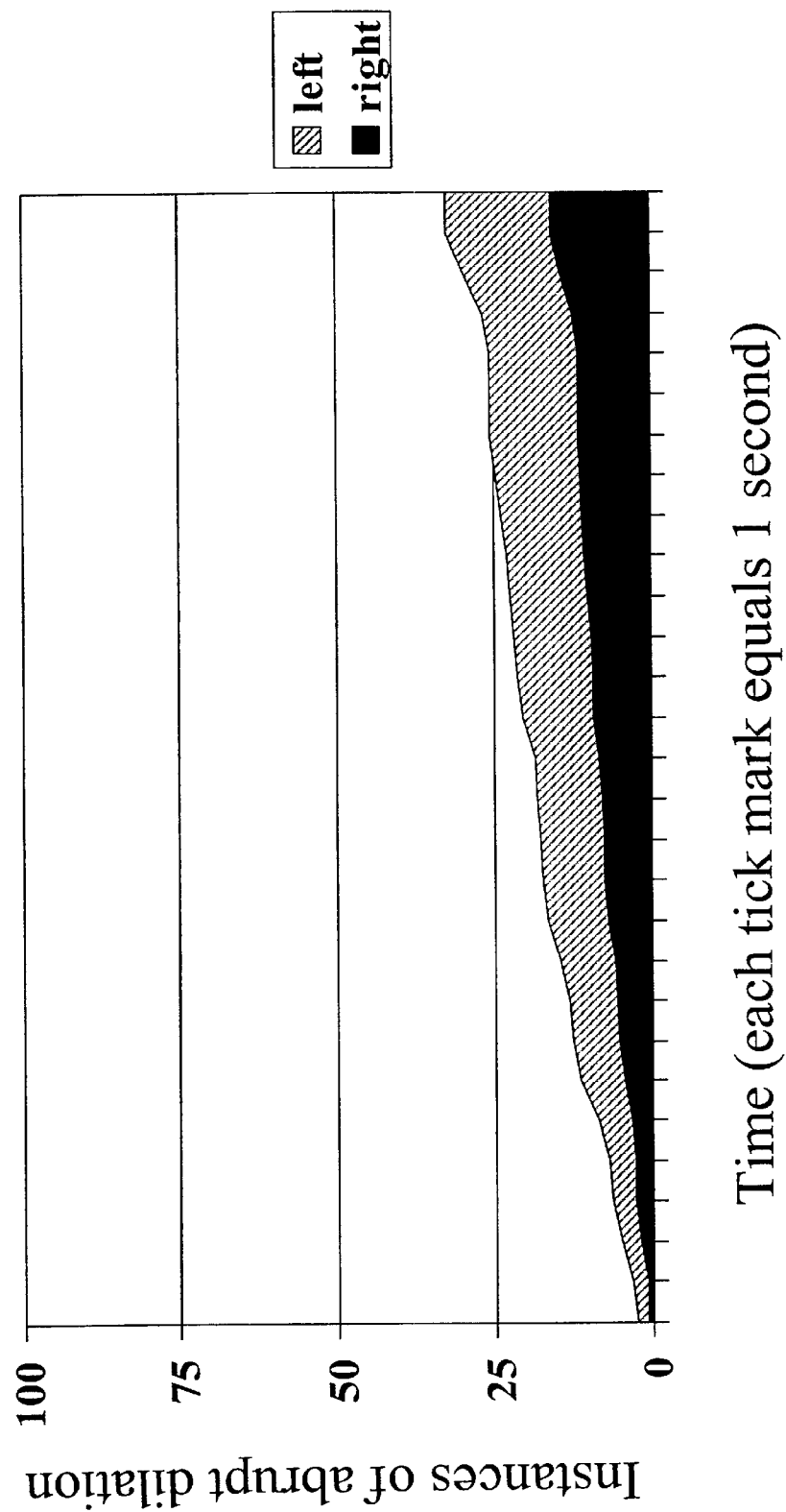

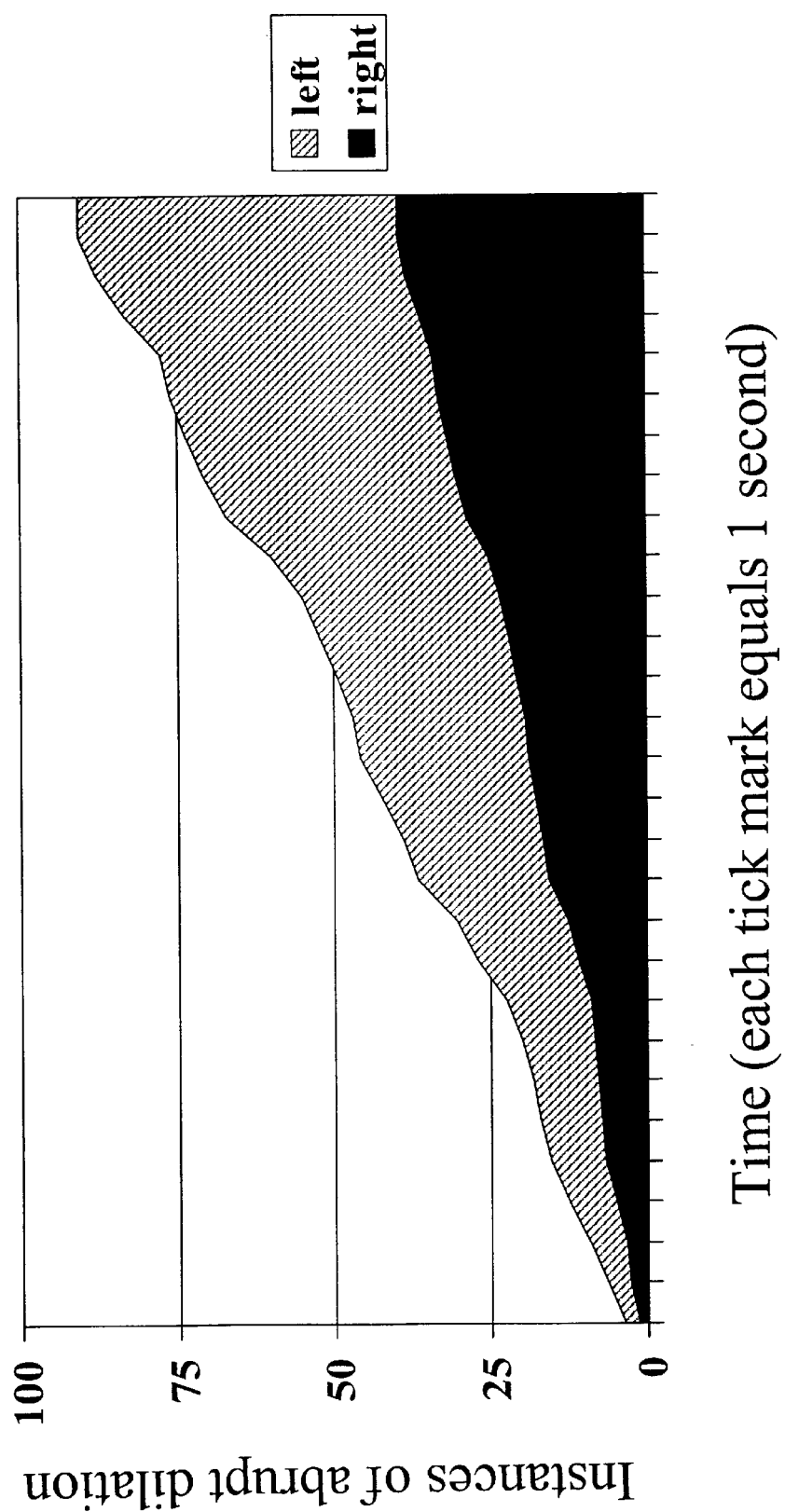
Figure 2: high level of aversion (cumulative levels of dilation)

METHODS FOR MONITORING AFFECTIVE BRAIN FUNCTION

TECHNICAL FIELD

The present invention relates to the evaluation of affective brain function and, more particularly, to the monitoring of such function as an indication of the reception of visual stimulus.

BACKGROUND OF THE INVENTION

The human response to visual stimulation involves a complex system of physiological and neurological systems. In the field of advertising and website design, as well as other fields where emotional responses to visual stimulus are as important than cognitive responses, there is a desire to measure the former and distinguish between the two using objective criteria.

It has long been recognized that certain physiological responses, such as pupillary changes, are associated with cognitive activity (Ahern, S. and Beatty, J. (1979) Science 205: 1289–1292). Monitoring of such changes is considered important in analyzing the usefulness of a visual display and its effectiveness in providing an efficient roadmap to desired information. For example, U.S. Pat. No. 6,090,051 describes a method of analyzing cognitive activity as a function of mathematically normalized pupillary responses to visual stimuli, such as viewing webpages. These methods are important to the analysis of cognitive analytical functions, such as arithmetics, sentence functioning and language skills, but are not as closely correlated to the analysis of affective neurological functions, such as the likeability of a particular visual stimulus or the aversive impact of a disagreeable stimulus.

Pupil dilation is primarily the result of the integrated activity of two groups of muscles located on the iris. One set of muscles (the circular muscles) encircles the pupil: when activated, this set of muscles serves to constrict the diameter of the pupil and make it smaller. The second set of muscles (the radial muscles) lies immediately outside the circular muscles and extends radially from the pupil out through the iris. When activated, the radial muscles pull the pupil diameter outward and cause it to become larger. These two sets of muscles typically work together through reciprocal innervation, a physiological process involving both agonistic and antagonistic responses. The result of this process is a response larger than either set of muscles alone could produce.

When stimulated by light, the pupil responds by oscillating its size. Insofar as this response results in changes in pupil diameter, this response has been extensively studied. During the light reflex, the circular muscles act as the agonist and are stimulated to contract, while the radial muscles act as the antagonists and are inhibited from dilating the pupil. The reflex is fleeting, and can be measured as a pulsing of the pupil (Lowenfield, in "The Pupil: Anatomy, Physiology and Clinical Applications, Vol. I; Ames, Iowa, Iowa State University Press.)

When an individual's pupillary response to visual stimulus is measured as a way of assessing the effectiveness of visual input requiring cognitive processing, the pupillary response is recorded and processed in a manner that allows one to distinguish it from a simple light response as described in U.S. Pat. No. 6,090,051. Such measurements, and post-processing thereof, are specifically designed to analyze "tasks" associated with effortful cognitive processing. These methods are distinct from other related methods that are designed to do the opposite, i.e. correlate measured eye movements to assumed cognitive activity as described in U.S. Pat. No. 6,102,870. In other words, whereas the '051 patent describes methods to evaluate cognitive activity, i.e. thought processes, in response to visual stimulus, the '870 patent describes methods to correlate visual responses to thought processes, i.e. "mental states", which are predetermined to be associated with such responses. Accordingly, the '051 patent focuses prospectively on designing ways to alter visual stimulus to optimize the cognitive response, while the '870 patent focuses retrospectively on characterizing visual effects as being indicative of predetermined mental states.

In comparison to such methods that are specifically designed to evaluate cognitive workload, the present patent application provides methods for, inter alia, evaluating affective, or emotional, non-cognitive responses to visual stimulus. The cognitive response is perhaps more important in fields such as training videos, visual learning methods and other such "thinking" tasks, the non-cognitive response may be more important in fields such as television and computer advertising, and the computer game industry, the commercial success of which is most influenced by immediate emotional responses to visual stimulus.

It has long been recognized that the brain is highly lateralized, in that the two halves of the brain are not exactly alike. In fact, both sides of the brain, or "hemispheres", have certain functional specializations that appear to be localized in one-half of the brain. As far back as the 1800s, Paul Broca, a French neurosurgeon, suggested that the left hemisphere was associated with an analytical skill such as language. Since then, many other investigators have determined that there is a relationship between "handedness" (i.e. an individual writes primarily with their right or left hand) and brain hemisphere function.

There is a wide body of scientific literature that describes that, in general, the left brain hemisphere is associated more with linear, logical, analytical, and unemotional thinking, whereas the right brain is associated more with spatial, creative, emotional and intuitive thinking. Although such generalizations are still not fully understood at a neurophysiological level, this literature and the studies associated therewith provide impetus for the design of systems to measure physical responses to visual stimulus that are selectively associated more with a "right brain" response than a "left brain" response.

More specifically, the present invention describes the unexpected discovery that the abrupt pupillary changes that were, in part, previously attributed to "noise" during the measurement of pupillary responses are actually meaningful and extremely useful measurements of affective brain responses.

BRIEF DESCRIPTIONS OF THE DRAWINGS

FIG. 1 depicts the results of Experiment 1 when an advertisement having a high likeability rating is being viewed by test subjects.

FIG. 2 depicts the results of Experiment 2 when an advertisement having a high aversion rating is being viewed by test subjects.

DISCLOSURE OF THE INVENTION

The present invention relates to a method for assessing the response of a subject to visual stimulus which includes monitoring pupillary response of the subject during exposure to visual stimulus using a suitably adapted apparatus and translating the pupillary response into data representative of abrupt changes in pupil diameter. Such abrupt changes are indicative of a person's affective and cognitive response to the visual stimulus. A change is considered "abrupt" if the pupil size increases by 5% or more in less than 20 milliseconds.

The method of the present invention also may involve calculating a dilation index based on the abrupt changes in pupil diameter.

Although in one embodiment, only one eye need be monitored, such as the left eye, in other embodiments, it may be desirable to measure the pupillary response in both eyes simultaneously.

In another aspect of the present invention, the method further involves subjecting the data to wavelet analysis to eliminate light reflex responses.

The method of the present invention can be used to monitor many different types of visual stimuli, which are both static (e.g. print advertisements or web sites) as well as non-static (e.g. television advertisements.)

In a further aspect of the present invention, the pupillary response data representative of changes in pupil diameter is used to generate a dilation index over a given time frame, such as the entire time of the study, or any increments thereof.

Other objects, features and advantages of the present invention will become apparent from the following detailed description.

DETAILED DESCRIPTION OF THE INVENTION

The present invention involves the correlation of the pupillary response of a subject to visual stimulus that can be selectively indicative of an affective (non-cognitive) response. The term "affective response" as used herein refers to a response that indicates affective, emotional, activity of a subject. Such responses can be measured by designing studies that measure right-brain associated stimulus. Accordingly, one way of minimizing responses associated with cognitive activity is simply to measure visual responses of only the left eyes of normal subjects.

In a preferred embodiment, the present method involves monitoring the pupillary response of both eyes simultaneously during exposure to visual stimulus, then studying the differential changes in each eye as described below.

In one important aspect of the present invention, the method involves monitoring the pupillary response of a subject challenged with visual stimulus, recording the pupillary response, subjecting such recorded pupillary response to wavelet analysis in order to measure true pupillary responses and not just light reflexes, and thereafter determining the incidence of abrupt pupillary dilation.

Pupillary response can be measured using a variety of commercially available apparatuses, such as the EyeLink System, distributed by SensoMotoric Instruments, which measures both pupil changes and eye movement, as well as similar apparatuses that are customized for the instant application using well know mechanical techniques. Many pupillometers are available that measure only pupil changes without eye tracking capabilities.

The dilation reflex that results in abrupt pupil dilation is a transitory event, which is observed predominately as a pulsing of the diameter that, unlike the light response, is irregular and sharp, often exhibiting large jumps followed by rapid declines. Accordingly, any method of differentiating between dilation reflex and light reflex can be used in the practice of the present invention.

Data collection and initial processing are described in U.S. Pat. No. 6,102,870. Depending on the type of visual stimulus (e.g. advertisements that span a lot of time, such as a video, or a static advertisement, such as a snapshot of a commercial product), wavelet results are further processed accordingly. For example, for non-static visual stimulus, a value is assigned that corresponds to the number of instances of high pupil activity, or abrupt dilation, per second for each eye, i.e. the "dilation index". It should be understood that this dilation index is a measure of the change in pupil diameter, which may be expansion or contraction. Although measurements may be taken every second, it is also understood that other time frames may equally be suitable, such as every 2 to 5 seconds, or every ⅓ or ½ second, and so on. This index forms the basis for subsequent measurements.

Once the indexes are calculated for both eyes as a function of time, additional mathematical analysis is performed using known statistical methods. For example, the relative index is determined over time. If the visual stimulus requires significant cognitive effort, the right eye index will be substantially larger than the left eye index, typically by a factor of 2 or 3 but occasionally up to 10 times greater. If the visual stimulus elicits an affective, emotional response, the left eye index is as great or greater than the right eye index, with the difference being small for positive affective response and considerably larger for negative affective response.

In addition, the changes in the dilation index of the left eye alone over time can be determined. If the visual stimulus is considered likeable, the dilation index over time will increase to a lesser extent than if the visual stimulus is considered aversive. Accordingly, one approach to adapting the present method to the evaluation of the affective response to visual stimulus is to selectively measure the pupillary response of the left eye as a more effective means of evaluating the right-brain associated response to visual stimulus. Such approaches are more than adequate when the evaluation involves a number of subjects whose left-brain vs. right-brain abnormalities can be normalized.

In other instances, such methods may necessarily involve prescreening of test subjects to assess left-brain vs. right-brain activity. For instance, asymmetric pupillary responses can be premeasured based on stimulus to the right or left eye, and subsequent test stimulus can be given only to the eye associated with more stimular arousal characteristically associated with an affective response. In particular, the association of handedness with response to exposure of right-handed individuals to visual stimulus is described in Cortex, 34(5): 753–762 (1998). As described therein, there was a three-phasic response to visual stimulus—an initial or first constriction, a subsequent dilation, then a second constriction. It appeared that there was more measured dilation when the exposure of visual stimulus was limited to the right side. Accordingly, one method for determining which eye to measure in order to assess characteristically "right-brain" associated non-cognitive activities is to measure the pupillary response of the eye that shows the least dilation response when challenged with a dilatatory stimulus. In yet other applications, it may be sufficient to subject the subject to a questionnaire to evaluate which eye to measure, which may include questions like, "Do you write with your left hand or your right hand?"

In addition to such methods for analyzing and quantifying the right-brain associated response to visual stimulus on a total stimulatory event basis, the present invention relates to methods of monitoring both the right and left pupillary response simultaneously, and correlating the response to predetermined or simultaneously evaluated left-eye and/or right-eye characteristics to select for right-brain associated responses. As such, for certain individuals who may exibit mixed pupillary responses to varying stimulus, it may be more appropriate to evaluate the left eye responses when the right eye is exhibiting a high activity index, and vice versa. Thus, the present invention provides for a real-time analysis method for capturing and evaluating the data that most effectively correlates with the response sought to be measured.

It will also be appreciated by one of skill in the art, that while the preferred embodiment is a method f selectively studying affective responses, the present invention can easily be adapted for studying cognitive responses, or the combination of the two, during visual stimulation.

Numerous modifications may be made to the foregoing invention without departing from the basic teachings thereof. Although the present invention has been described in substantial detail with reference to one or more specific embodiments, those of skill in the art will recognize that changes may be made to the embodiments specifically disclosed in this application, yet these modifications and improvements are within the scope and spirit of the invention as set forth in the claims which follow. All publications, patents, and patent applications cited in this specification are incorporated herein by reference as if each such publication, patent, or patent application was specifically and individually indicated to be incorporated herein by reference.

EXAMPLES

Example 1

This experiment consists of two separate studies. In the first study, a total of 62 advertisements were studied. These were presented in three sets of size 20, 21, and 21 to three different groups of 10 subjects. Each subject saw all advertisements in the set and then rated them for likability on a scale of 1–5.

The second study was based on a total of 55 advertisements, with 28 in one set and 27 in a second set. Each set was presented to a different group of 13 subjects, with each subject looking at all advertisements in the set and then responding to a survey that included measures of likability, recall, recognition, and persuasion.

The data were computed for each subject on each advertisement and then averaged to produce values for each advertisement. The initial step of data processing was to determine the pupillary responses for each eye separately over each advertisement after blink artifacts were removed using the process described in U.S. Pat. No. 6,102,870. Next, the exact times that the dilation instances occurred were found and tallied. These results are depicted in FIGS. 1 and 2.

An alternative to the graphical analyses in FIGS. 1 and 2 that are presented in one second intervals, a dilation index can also be determined during different time periods, for example, the first 25% of the advertisement, the second 25% of the advertisement, the third 25% of the advertisement, and the final 25% of the advertisement. (Note: quarters were chosen arbitrarily as the unit of measure. Other means of breaking the advertisement into time chunks would be equally appropriate.)

Once the number of instances were determined for each quarter, the index of instances per second per quarter were computed. These are the basis for most of the subsequent measures used in the analysis. The measures investigated are as follows:

The average index per quarter for each advertisement for each eye

A set of differences between the eyes and across the quarters for each eye

A set of ratios between the eyes and across the quarters for each eye

Squared measures of the above to test for quadratic effects

For each set of advertisements studied, a significant relationship was found among the the left eye dilation measure, the right eye dilation measure, and the affective response of the subject to each advertisement. In general, this experiment demonstrates that advertisements which were well liked had the following characteristics:

The left eye showed slightly but consistently more abrupt shifts in dilation than the right eye;

The dilation measures for both eyes increased slowly but steadily across the duration of the advertisement;

The total dilation measures across both eyes fell in the range of 1–2 abrupt changes per second.

In contrast, the ads that were actively disliked had the following characteristics:

The left eye showed a great deal more abrupt shifts in dilation than the right eye, especially in the latter seconds of viewing the advertisement;

The change in the left eye dilation measure over the course of the advertisement was larger than the change in the right eye dilation measure;

The total dilation measures across both eyes either were extremely low (less that 1 episodes per second) or extremely high (greater than 2 episodes per second).

These results are depicted in FIGS. 1 and 2, which show the cumulative dilation measures for both eyes across the duration of the advertisement. The measures are averages taken across all subjects who viewed these two advertisements. From FIGS. 1 and 2, two trends can be seen. First, the most striking result is the fact that the cumulative record of instances for both eyes combined is negatively correlated with advertisement preference. That is, the advertisements that were liked the least caused the greatest number of dilations. However, there appears to be a critical level of activation that advertisements need to engender in order to be liked. Thus, there is a quadratic effect in which very low and very high instances of activity indicate dislike. Moderate levels are found for advertisements that were liked.

The second finding concerns the relationship between the right and left eye. Advertisements that were liked, generally, had the same pattern of cumulative responses, taken second by second, across the full duration of the advertisement. But, for the vast majority of advertisements that were liked, the left index was greater than the right index. Again, there appears to be a quadratic effect. When the left index is less than the right index or when the left eye is substantially greater than the right eye (which shows up in the last several seconds of the cumulative plots), the ads were less well liked than when the left eye maintained a small but constant advantage relative to the right eye.

These findings based on pupil dilation have been compared to the ratings given the advertisements by the individuals who viewed them. A logistic regression analysis shows that the methods described herein can be used to predict with 85% accuracy whether the advertisements were liked or disliked, using several ratio and difference variables to capture the main characteristics described above. These findings also correlate quite well with national rankings of these same advertisments. It is therefore clear that pupil dilation changes are related to the affective response the individual has to the visual material.

I claim:

1. A method for assessing a sensory response of a subject to visual stimulus, comprising the steps of:
   a) monitoring pupillary response of the subject during exposure to visual stimulus using a suitably adapted apparatus; and
   b) translating the pupillary response into data representative of abrupt changes in pupil diameter, wherein abrupt changes are defined by a change in pupil size by 5% or more in less than 20 milliseconds.

2. The method of claim 1 further comprising the step of calculating a dilation index based on the abrupt changes in pupil diameter.

3. The method of claim 1, wherein step a) further comprises monitoring left and right pupillary responses of the subject.

4. The method of claim 1, wherein step a) further comprises monitoring left pupillary response of the subject.

5. The method of claim 1, wherein step b) further comprises subjecting the data to wavelet analysis to minimize light reflex responses.

6. The method of claim 1, wherein the visual stimulus is non-static and step a) further comprises monitoring pupillary response over time.

7. A method for assessing sensory response of a subject to visual stimulus over a period of time being divisible by a number of equal time increments, comprising the steps of:
   a) monitoring left and right pupillary response of the subject during exposure to visual stimulus using a suitably adapted apparatus, wherein said pupillary response includes a plurality of dilation reflexes;
   b) translating the pupillary response into data representative of the dilation reflexes; and
   c) converting the data into a measure of the sensory response over time by calculating an average dilation index during each of said time increments, wherein said dilation index comprises a measure of the dilation reflexes each of the time increments.

8. The method of claim 7, wherein the number of time increments is between 2 and 100.

9. The method of claim 8, wherein the number of time increments is 4.

10. The method of claim 7, wherein step c) further comprises determining the difference between the average dilation index in the right and left eye during each of said time increments.

11. The method of claim 7, wherein step c) further comprises determining the ratio between the average dilation index in the right and left eye during each of said time increments.

12. A method for categorizing a visual stimulus as attractive or aversive, comprising the steps of:
   a) monitoring left eye pupillary responses of a subject during exposure to the visual stimulus over a given time period using a suitably adapted apparatus; and
   b) translating the pupillary response into data representative of abrupt changes in pupil diameter;

wherein the visual stimulus is categorized as attractive if the left eye demonstrates an average number of abrupt changes per second that is equal to or between one and two, and aversive if the left eye demonstrates an average number of abrupt changes per second that is less than one or more than two.

* * * * *